US012740790B2

(12) United States Patent
Nakagawa

(10) Patent No.: US 12,740,790 B2
(45) Date of Patent: Sep. 22, 2026

(54) BONE REMOVER

(71) Applicant: Medmetalex Co., Ltd., Osaka (JP)

(72) Inventor: Tomomi Nakagawa, Osaka (JP)

(73) Assignee: Medmetalex Co., Ltd., Osaka (JP)

( * ) Notice: Subject to any disclaimer, the term of this patent is extended or adjusted under 35 U.S.C. 154(b) by 0 days.

(21) Appl. No.: 18/697,614

(22) PCT Filed: Nov. 28, 2023

(86) PCT No.: PCT/JP2023/042534

§ 371 (c)(1),
(2) Date: Apr. 1, 2024

(87) PCT Pub. No.: WO2024/252693

PCT Pub. Date: Dec. 12, 2024

(65) Prior Publication Data

US 2026/0151142 A1 Jun. 4, 2026

(30) Foreign Application Priority Data

Jun. 9, 2023 (JP) ................................ 2023-095489

(51) Int. Cl.
*A61B 17/16* (2006.01)

(52) U.S. Cl.
CPC ................................ *A61B 17/1655* (2013.01)

(58) Field of Classification Search
CPC . A61B 17/16; A61B 17/1613; A61B 17/1615; A61B 17/1635; A61B 17/164; A61B 17/1655; A61B 17/1657; A61B 17/1659; B23G 5/06; B23G 5/14; B23G 5/16
See application file for complete search history.

(56) References Cited

U.S. PATENT DOCUMENTS 4,978,350 A * 12/1990 Wagenknecht .... A61B 17/8635 411/387.7
6,068,632 A * 5/2000 Carchidi ............ A61B 17/1635 433/165
6,197,031 B1 * 3/2001 Barrette ............... A61B 17/164 606/311

(Continued)

FOREIGN PATENT DOCUMENTS

CN 110226971 A * 9/2019 ........... A61B 50/312
CN 214595952 U 11/2021

(Continued)

*Primary Examiner* — Eric S Gibson
(74) *Attorney, Agent, or Firm* — Howson & Howson LLP

(57) ABSTRACT

A bone remover for removing bones such as a femoral bone head in a minimally invasive surgical procedure comprises a shaft having a handle at a proximal end, a screw portion at a leading end and tapered toward the leading end, and a blade portion at the leading end of the screw portion. Helical threads of the screw portion are on a surface of, and coaxial with, the shaft. The blade portion is plate-shaped and tapered toward the leading end, and has a cutting blade attained by at least one raked surface formed in a lateral end portion. A proximal side of the raked surface and a top surface at the leading end of the threaded portion are either directly connected, or connected by an extension surface at the proximal end of the raked surface and the top surface at the leading end of the threaded portion.

2 Claims, 8 Drawing Sheets

(56) References Cited

U.S. PATENT DOCUMENTS 6,312,432 B1 * 11/2001 Leppelmeier ...... A61B 17/1615 408/230
D544,892 S * 6/2007 Watson ........................ D15/139
7,267,514 B2 * 9/2007 Wetzl ...................... B23B 51/02 408/230
D585,919 S * 2/2009 Cantlon ....................... D15/139
7,665,989 B2 * 2/2010 Brajnovic ............ A61C 8/0089 433/165
8,128,671 B2 * 3/2012 Taylor .................. A61B 17/863 606/315
8,460,328 B2 * 6/2013 Piferi ..................... A61B 90/39 606/180
8,814,914 B2 * 8/2014 Miller ................ A61B 17/3472 606/279
9,198,743 B2 * 12/2015 Wang ................... A61C 8/0089
D774,878 S * 12/2016 Ouyang ......................... D8/387
10,136,902 B2 * 11/2018 Farris ................. A61B 17/1655
10,603,049 B2 * 3/2020 Bake .................. A61B 17/1635
11,039,842 B1 * 6/2021 Bennett ................ A61B 17/164
D1,032,837 S * 6/2024 Stroh ........................... D24/146
12,043,488 B2 * 7/2024 Naglapura .......... F15B 15/1447
12,127,748 B2 * 10/2024 Ng ................... A61B 17/06166
2003/0018337 A1 * 1/2003 Davis ................. A61B 17/1655 606/80
2005/0070907 A1 * 3/2005 Abernathie ........ A61B 17/1655 606/80
2005/0149031 A1 * 7/2005 Ciccone ............. A61B 17/1615 606/280
2007/0055249 A1 * 3/2007 Jensen ............... A61B 17/8863 606/288
2007/0162018 A1 * 7/2007 Jensen ............... A61B 17/8863 606/326
2007/0259314 A1 * 11/2007 Danger .................... A61C 3/02 433/165
2008/0051793 A1 * 2/2008 Erickson ............ A61B 17/1671 606/279
2010/0030218 A1 * 2/2010 Prevost .................. A61B 17/17 606/80
2010/0324562 A1 * 12/2010 Thomsen ........... A61B 17/1604 606/80
2012/0191097 A1 * 7/2012 Jorneus ............. A61B 17/1655 606/80
2012/0245585 A1 * 9/2012 Kaiser ................ A61B 17/1633 606/80
2014/0100575 A1 * 4/2014 Yim ................... A61B 17/1655 606/80
2014/0113245 A1 * 4/2014 Heo ..................... A61C 8/0068 433/75
2014/0224070 A1 * 8/2014 Bake ..................... A61F 2/3872 76/108.1
2016/0151076 A1 * 6/2016 Bake ..................... A61F 2/4684 606/80
2017/0027592 A1 * 2/2017 Farris ................. A61B 17/1615
2019/0105060 A1 * 4/2019 Sommers ........... A61B 17/8645
2021/0322028 A1 * 10/2021 Ng ................... A61B 17/06166

FOREIGN PATENT DOCUMENTS

CN 119486673 A * 2/2025 ......... A61B 17/1655
EP 4505955 A1 * 2/2025 ......... A61B 17/1655
FI 110575 B * 2/2003 ......... A61B 17/1655
JP 2018108224 A * 7/2018
JP 7398850 B1 * 12/2023 ......... A61B 17/1655
JP 2024176725 A * 12/2024 ......... A61B 17/1655
WO WO-2024252693 A1 * 12/2024 ......... A61B 17/1655

* cited by examiner

BONE REMOVER

FIELD OF THE INVENTION

The present invention relates to bone removers used in surgery.

BACKGROUND OF THE INVENTION

In orthopedics and the like, for example, in total hip replacement, a bone (such as a femoral bone head) is cut and removed. In such a case, because the femoral bone head is deep within the body, a bone head remover is used. FIG. 7 shows a bone head remover depicted in FIG. 6 of Chinese Utility Model Publication No. CN214595952. A bone head remover 100 is composed of a handle portion 101, a shaft portion 102, and a tapered screw portion 103. The femoral bone head is removed from the surgical field by screwing and engaging the tapered screw portion 103 into the femoral bone head.

FIG. 8 shows a bone head remover depicted in FIG. 1 of Chinese Utility Model Publication No. CN214595952. A bone head remover 200 is composed of a handle portion 201, a shaft portion 202, and a winged blade 203. The femoral bone head is removed from the surgical field by inserting and engaging the winged blade 203 into the femoral bone head.

SUMMARY OF THE INVENTION

A surface of a bone is covered with a hard cortical bone and an inside is composed of soft, spongy bone. In using a bone head remover such as those depicted in FIGS. 7 and 8, it is common to insert from the spongy bone into a cut surface in the bone head. When the bone head remover is inserted into the femoral bone head from a cervical cutting line, it is necessary to expand the surgical field, and the length of the skin incision line becomes longer.

When the length of the skin incision line is shortened to implement minimally invasive surgery (MIS), and the bone remover is screwed in from the cortical bone into the surface of the femoral bone head, the bone remover cannot be inserted and engaged into the bone due to the high hardness of the cortical bone.

The present invention is made in view of such a problem. An object of the present invention is to provide a bone remover that can easily remove bones such as the femoral bone head even in a surgical procedure such as MIS.

The bone remover according to the present invention for solving the problem described above has an excellent function in that it can be inserted and engaged into the bone from the bone surface.

According to a first aspect of the present invention, a bone remover comprises a shaft portion, a handle portion disposed at a proximal end of the shaft portion, a tapered screw portion formed at a leading end of the shaft portion and tapered toward the leading end, and a blade portion disposed at the leading end of the tapered screw portion. The tapered screw portion has a helical threaded portion formed on a surface of a shaft that is coaxial with the tapered screw portion, the blade portion is a plate-shaped body tapered toward the leading end, and has a cutting blade attained by at least one raked surface formed in a lateral end portion. A proximal side surface of the at least one raked surface and a top surface at the leading end of the threaded portion are directly connected, or an extension surface at the proximal end of the at least one raked surface and the top surface at the leading end of the threaded portion are directly connected.

In this first aspect of the present invention, a bone remover comprises a shaft portion, a handle portion disposed at a proximal end of the shaft portion, a tapered screw portion formed at a leading end of the shaft portion and tapered toward the leading end, and a blade portion disposed at the leading end of the tapered screw portion, wherein the tapered screw portion has a helical threaded portion formed on a surface of a shaft that is coaxial with the tapered screw portion, the blade portion is a plate-shaped body tapered toward the leading end, and has a cutting blade attained by a raked surface formed in a lateral end portion, A proximal side surface of the at least one raked surface and a top surface at the leading end of the threaded portion are directly connected, or an extension surface at the proximal end of the at least one raked surface and the top surface at the leading end of the threaded portion are directly connected, so that the blade portion can easily perforate a cortical bone, the blade portion can drill sharp holes, and the tapered screw portion connected by the ridge line from the blade portion can penetrate into the cortical bone without slowing down.

In conventional products, the leading ends usually have a drill shape, which is suitable for drilling thin holes or holes in spongy bone, but the more they are inserted into hard cortical bone, the less driving force they have. The reason that the phrase "a proximal side surface of the at least one raked surface" is used here is because there are two raked surfaces, and, if the helical threaded portion is a double helix, it may be connected at two places. There may also be three or four places that are connected.

In a second aspect of the present invention, in a bone remover according to the first aspect of the invention, notches for self-tapping are formed in an axial direction on the threaded portion.

In this second aspect of the present invention, notches for self-tapping are formed in the axial direction on the threaded portion, so that, after the blade portion is inserted into the spongy bone from the cortical bone, the cortical bone can be self-tapped at these notches when the tapered screw is applied to the cortical bone, and the bone remover can be more easily inserted and engaged into the bone.

According to the present invention, a bone remover can be provided that can easily remove bones such as the femoral bone head, even in a surgical procedure such as MIS or the like.

DETAILED DESCRIPTION

Embodiments of the present invention will now be described in detail with reference to the drawings. The embodiments described below are essentially preferred examples, and are not intended to limit the scope or the spirit of the present invention, its applications, or its uses.

Figure 1:
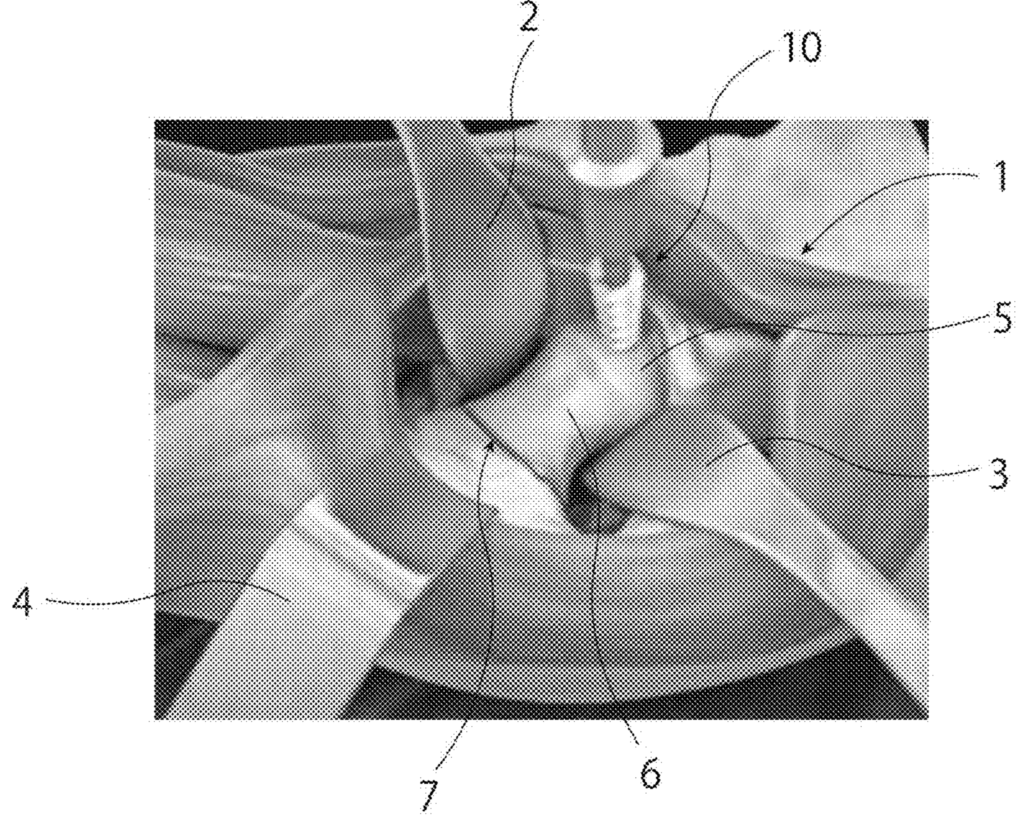
FIG. 1 is a schematic view of a femoral bone head being removed in hip prosthesis surgery using a bone remover of a first embodiment of the present invention.

FIGS. 1 to 5 show a bone remover in a first embodiment of the present invention. FIG. 1 shows a femoral bone head 5 being removed using a bone remover 10 of the first embodiment. In surgery, a scalpel is used to incise the skin, and a retractor hooks 2, 3, and 4 are used to form a surgical field 1. The femoral bone head 5 is cut with an electric blade saw or the like at an osteotomy line 7 on a femoral neck 6. The bone remover 10 is screwed into the cortical bone of the femoral bone head 5. If the bone remover 10 is pulled after the bone remover 10 is adequately screwed into the femoral bone head 5, the femoral bone head 5 can be removed from the patient's body.

Figure 2:
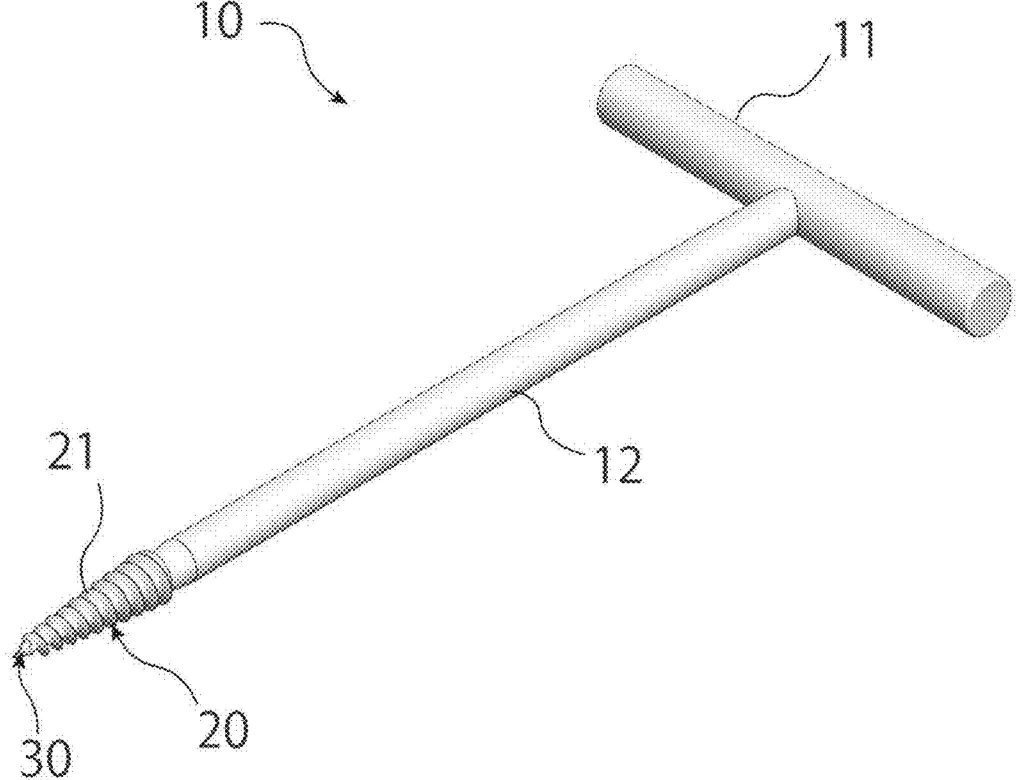
FIG. 2 is a perspective view of the bone remover in accordance with the first embodiment of the present invention.

FIG. 2 is a perspective view of the bone remover 10 in the first embodiment of the present invention. The bone remover 10 is equipped with a handle portion 11 for rotating a shaft portion 12, and for rotating and pressing a tapered screw portion 20. The handle portion 11 and the shaft portion 12 are T-shaped. However, they are not necessarily limited to this shape. The invention is applicable to bone removers that use a power source for rotation instead of being rotated by hand.

A tapered screw portion 20 is formed at the leading end of the shaft portion 12. The tapered screw portion 20 has a helical threaded portion 21 formed on a surface of a shaft 25 (see FIG. 4), which is coaxial with the tapered screw portion 20. A blade portion 30 is disposed at a leading end of the tapered screw portion 20.

Figures 3A, 3B:
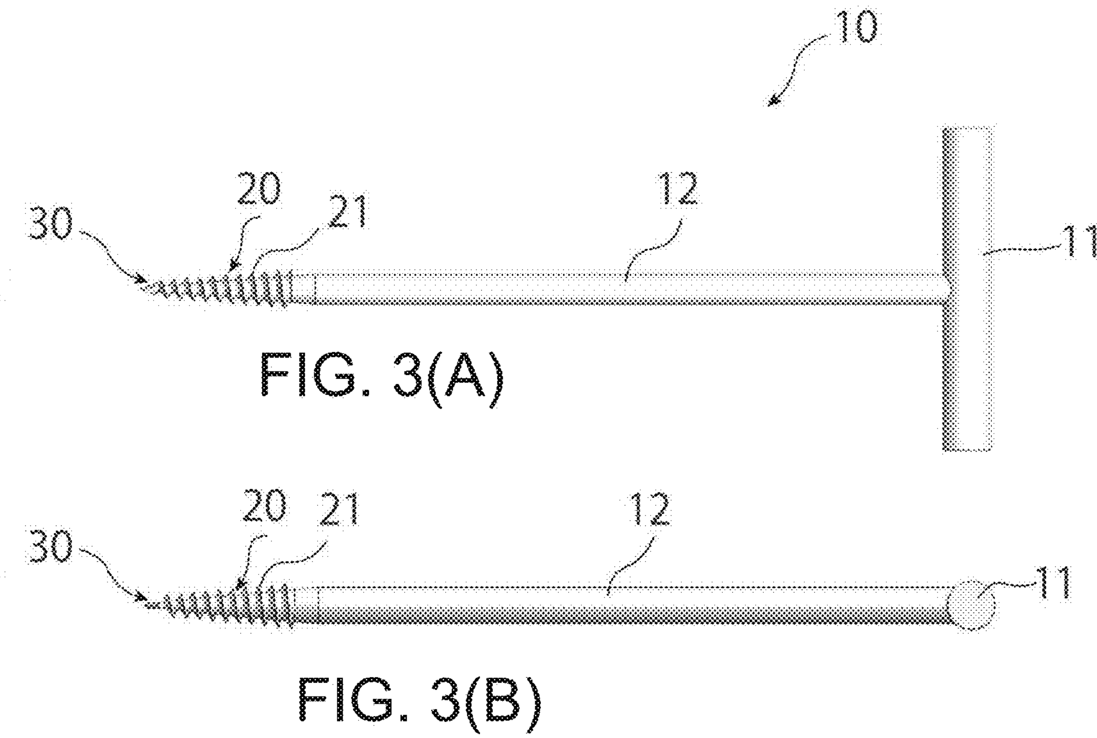
FIGS. 3(A) and 3(B) are, respectively, a plan view and a front view of the bone remover of the first embodiment of the present invention.

FIG. 3(A) is a plan view and FIG. 3(B) is a front view of the bone remover 10 in the first embodiment of the present invention. The bone remover 10 is equipped with the handle portion 11, the shaft portion 12, the tapered screw portion 20, the threaded portion 21, and the blade portion 30.

Figure 4:
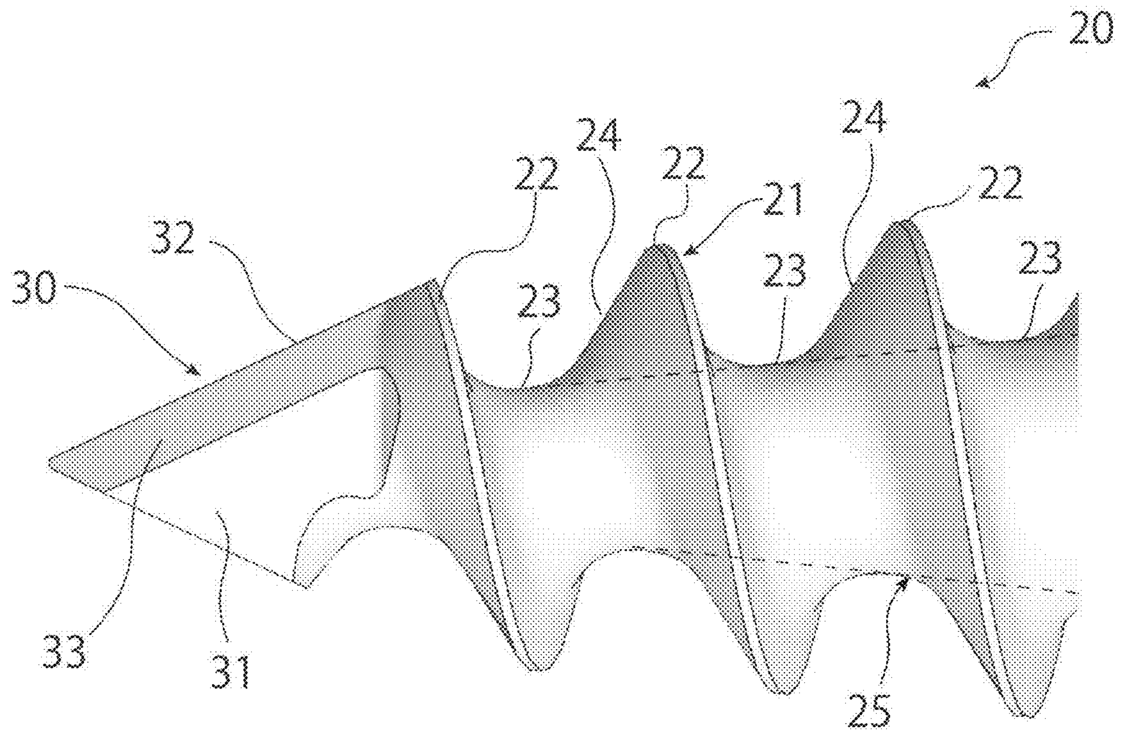
FIG. 4 is a plan view showing a leading end portion of the bone remover of the first embodiment of the present invention.

FIG. 4 is a plan view showing the leading end portion of the bone remover in accordance with the first embodiment of the present invention. This shows the leading end side portion and the blade portion 30 of the tapered screw portion 20. The threaded portion 21 of the tapered screw portion 20 is composed of a bottom surface 23 at the surface of the shaft 25, a slope surface 24 contiguous with the bottom surface 23, and a top surface 22 contiguous with the slope surface 24. In the blade portion 30, a first cutting blade 32 and a first flank surface 33 are formed on a plate-shaped body 31 the leading end of which is a tapered plate-shaped body.

In the first embodiment, there is one plate-shaped body 31, but there may be variations in which two plate-shaped bodies intersect at right angles, or in which there are cutting blades at four locations. The number of plate-shaped bodies may be three, four, or more.

Figure 5:
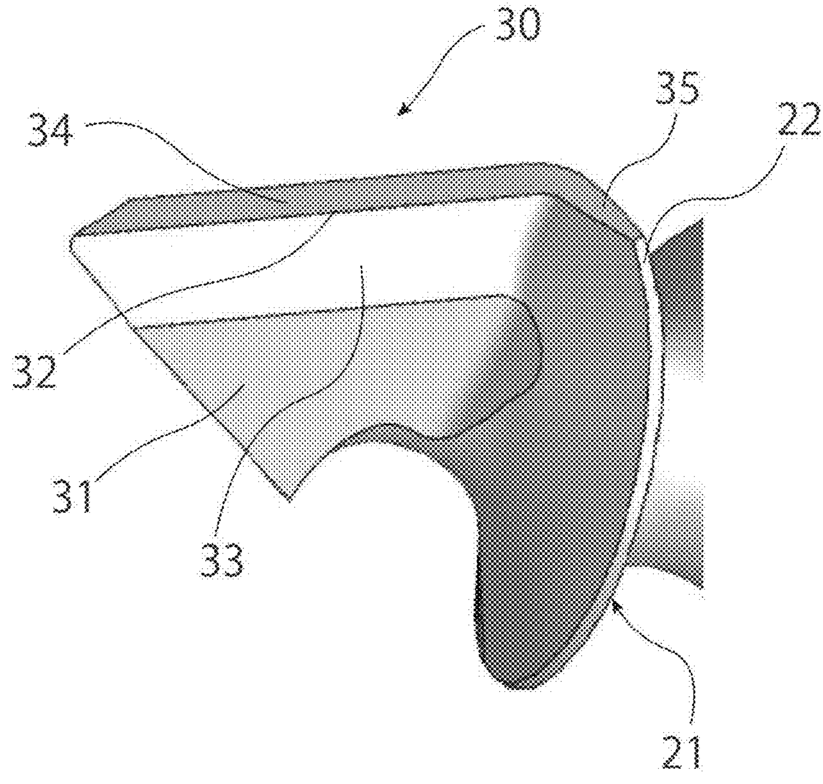
FIG. 5 is a perspective view showing the leading end portion of the bone remover of the first embodiment of the present invention.

FIG. 5 is a perspective view showing the leading end portion of the bone remover in accordance with the first embodiment of the present invention. The blade portion 30 is formed with the first cutting blade 32 attained by a first raked surface 34 formed at the lateral end portion of the plate-shaped body 31. The first flank surface 33 is formed on a front side from the first cutting blade 32. The first raked surface 34 and the top surface 22 of the threaded portion 21 are connected by a connecting surface 35. Alternatively, the first raked surface can be directly connected to the top surface of the threaded portion.

With the structure depicted in FIG. 5, the blade portion 30 sharply perforates the cortical bone, and the tapered screw portion, connected to the blade portion 30 by the connecting surface 35, penetrates the cortical bone of the femoral head without slowing down. Also, cutting shavings from the bone cut using the first cutting blade 32 are efficiently discharged through the slope 24 and the bottom surface 23 of the threaded portion 21 shown in FIG. 4.

Figure 6:
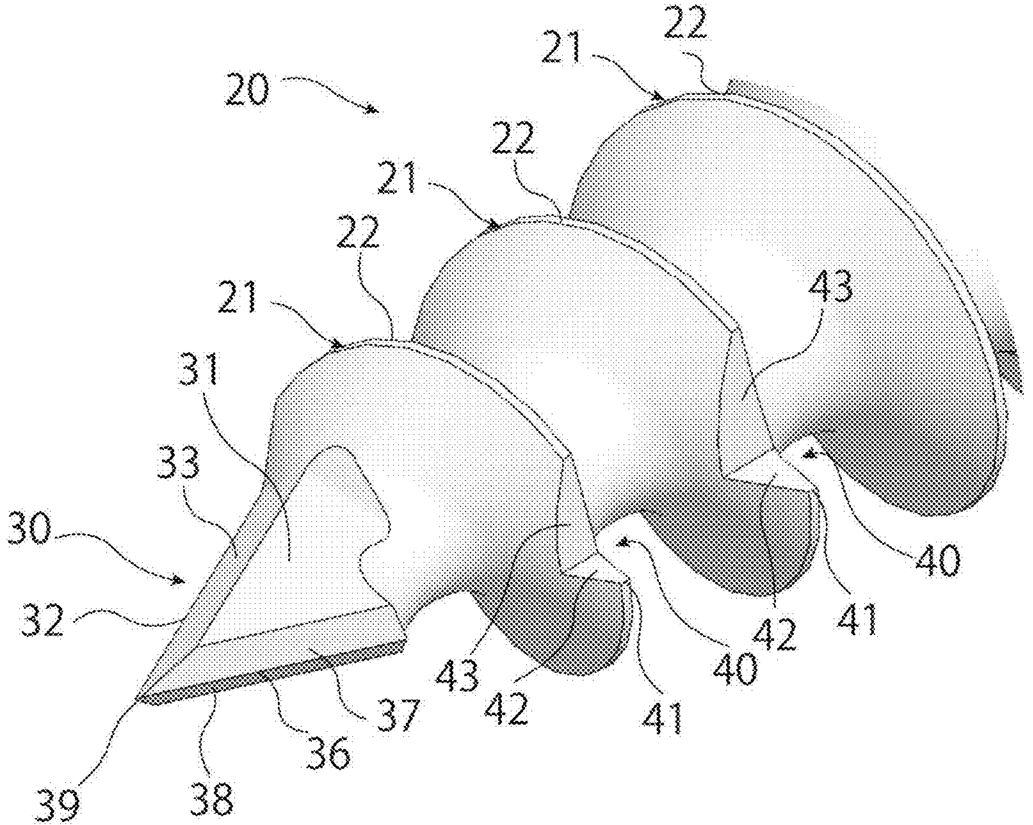
FIG. 6 is a perspective view showing a leading end portion of a bone remover according to a second embodiment of the present invention.
Figure 7:
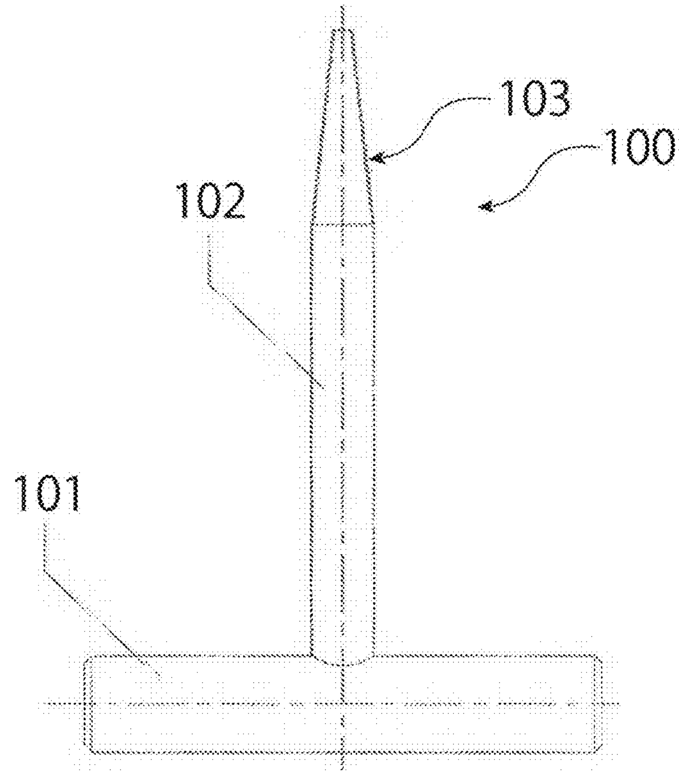
FIG. 7 is a plan view of a conventional bone remover described in Chinese Utility Model Publication No. CN214595952.
Figure 8:
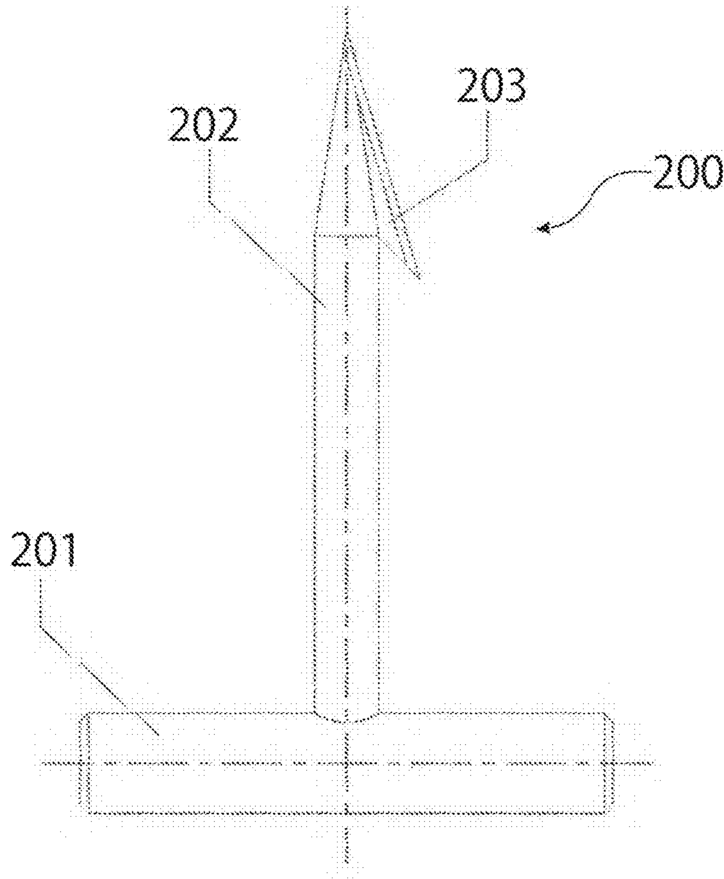
FIG. 8 is a plan view of another conventional bone remover described in Chinese Utility Model Publication No. CN214595952.

FIG. 6 is a perspective view showing a leading end portion of a bone remover in accordance with a second embodiment of the present invention. A blade portion 30 is formed at the leading end of a tapered screw portion 20. A second cutting blade 36 is formed by a second raked surface 37 and a second flank surface 38 opposite a first cutting blade 32. The first cutting blade 32 and the second cutting blade 36 intersect at an apex 39. The apex 39 is pushed into the cortical bone, and the cortical bone is drilled by the first cutting blade 32 and the second cutting blade 36.

The bone remover according to the second embodiment is characterized in that notches 40 for self-tapping are provided at the leading end of the tapered screw portion 20. The notches 40 are formed on the two threaded portions 21 at the leading end. The notch 40 may also be formed on an opposite side, i.e., at a location rotated 180° about the shaft axis, or notches may be provided at three or four locations spaced symmetrically about the shaft axis. The notch 40 has a first notch surface 42 and a second notch surface 43. A notch cutting blade 41 is formed at a boundary line between an outer surface 22 and the first notch surface 42. The existence of the notch cutting blade allows the cortical bone to be perforated by the notch cutting blade 41 when the cortical bone further remains after the cortical bone is drilled by the blade portion 30.

INDUSTRIAL APPLICABILITY

As described above, the bone remover according to the present invention can be suitably used as a bone remover that can easily remove bones such as the femoral bone head even in a surgical procedure such as MIS or the like.

REFERENCE SIGNS LIST

1; Surgical field
2, 3, 4; Retractor hook
5; Femoral bone head (bone)
6; Bone head and neck
7; Osteotomy line
10; Bone Remover
11; Handle portion
12; Shaft portion
20; Tapered screw portion
21; Threaded portion
22; Top surface
30; Blade portion
31; Plate-shaped body
32; First cutting blade
33; First flank surface

34; First raked surface
35; Connecting surface
36; Second cutting blade
37; Second raked surface
38; Second flank surface
39; Apex
40; Notch
41; Notch cutting blade
42; First notch surface
43; Second notch surface

What is claimed is:

1. A bone remover comprising:

a shaft portion;

a handle portion disposed at a proximal end of the shaft portion;

a tapered screw portion formed at a leading end of the shaft portion and tapered toward a leading end of the tapered screw portion; and a blade portion disposed at the leading end of the tapered screw portion, wherein the tapered screw portion has a helical threaded portion formed on a surface of a shaft that is coaxial with the tapered screw portion, said helical threaded portion having a leading end;

the blade portion is a plate-shaped body tapered toward a leading end of the blade portion, and has a cutting blade attained by at least one raked surface formed in a lateral end portion, said at least one raked surface having a proximal end; and a proximal side surface of said at least one raked surface and is connected to a top surface at the leading end of the helical threaded portion by a connection from the group consisting of a direct connection and a connection consisting of an extension of said at least one raked surface at the proximal end of said at least one raked surface, said extension being connected directly to said top surface at the leading end of the helical threaded portion.

2. The bone remover according to claim 1, wherein notches for self-tapping are formed in an axial direction on the helical threaded portion.

* * * * *